United States Patent [19]

Hughes et al.

[11] 3,951,621

[45] *Apr. 20, 1976

[54] PROCESS FOR SEPARATING ONE OR MORE COMPONENTS OF A GASEOUS MIXTURE

[75] Inventors: Robert D. Hughes; Edward F. Steigelmann, both of Park Forest, Ill.

[73] Assignee: Standard Oil Company, Chicago, Ill.

[ * ] Notice: The portion of the term of this patent subsequent to Sept. 11, 1990, has been disclaimed.

[22] Filed: May 30, 1973

[21] Appl. No.: 365,204

[52] U.S. Cl. .................................. 55/16; 55/158
[51] Int. Cl.² .................................. B01D 53/22
[58] Field of Search .......................... 55/16, 158

[56] References Cited
UNITED STATES PATENTS

| | | | |
|---|---|---|---|
| 3,172,741 | 3/1965 | Jolley | 55/16 |
| 3,396,510 | 8/1968 | Ward et al. | 55/16 |
| 3,758,605 | 9/1973 | Hughes et al. | 55/16 |

*Primary Examiner*—Charles N. Hart
*Assistant Examiner*—Robert H. Spitzer
*Attorney, Agent, or Firm*—Morton, Bernard, Brown, Roberts & Sutherland

[57] ABSTRACT

Novel separation film membranes are made with cross-linked hydrophilic polyvinyl alcohol and nylon, and the films contain complex-forming metal components which are active in the presence of water. The polyvinyl alcohol is cross-linked by reaction with a polycarboxylic acid. The invention includes the membranes, their method of manufacture, and the method of using them to separate one or more components of a gaseous mixture.

8 Claims, No Drawings

PROCESS FOR SEPARATING ONE OR MORE COMPONENTS OF A GASEOUS MIXTURE

This invention relates to hydrophilic, semi-permeable membranes containing complex-forming metals, comprising a polyamide and a cross-linked polyvinyl alcohol. The presence of the cross-linked polyvinyl alcohol serves to increase the hydrophilic properties of the membrane. The invention is further directed to the method of making the membranes which comprises dissolving polyvinyl alcohol and a cross-linking polycarboxylic acid in an aqueous dispersion containing nylon. A film is formed from the dispersion, and the polyvinyl alcohol is cross-linked by reaction with the polycarboxylic acid to fuse the polymer aggregates. This method avoids the problem of finding a solvent for both the nylon and cross-linked polyvinyl alcohol which arises when the polymers are merely physically mixed to form a solution which is made into a film. The invention is also directed to the use of the membranes in processes for separating one or more components from gaseous mixtures.

There is considerable commercial interest in separating components, e.g., aliphatically-unsaturated hydrocarbons, from mixtures containing such materials. These aliphatically-unsaturated hydrocarbons are reactive materials that serve in various roles, generally as intermediates in chemical syntheses. A number of the unsaturated hydrocarbons are employed as monomers in the formation of polymers and, in this regard, olefins such as ethylene, propylene, butadiene and isoprene are well known. These olefins, as well as other unsaturated materials, for instance, acetylene, are also used to form relatively low molecular weight products.

The aliphatically-unsaturated hydrocarbons are most often made available on a commercial basis in admixture with other chemical compounds, frequently other hydrocarbons. These unsaturated hydrocarbon-containing streams are usually by-products of chemical syntheses or separation processes. When the hydrocarbon streams are liquid under normal conditions or can readily be made so, ordinary distillation techniques can be used to separate the hydrocarbon components, providing they have sufficiently different boiling points for the process to be economically feasible. Especially when the hydrocarbon mixtures contain materials having close boiling points, which is frequently the case with hydrocarbons of the same number of carbon atoms or having a difference of only one carbon atom, distillation may not be an attractive separation procedure. In such cases, more expensive processes are often used and involve operations such as solvent extraction or extractive distillation which entail considerable expense, if indeed they are technically feasible in a given situation.

When the mixture containing the aliphatically-unsaturated hydrocarbon is essentially in a gaseous state at normal or ambient conditions of temperature and pressure, separation of the desired component from the mixture may be even more troublesome. In these situations, cryogenic processes may be used, but they are expensive. The components of these normally gaseous mixtures may not even have particularly close boiling points, but, nevertheless, the mixture must be cooled in order to separate one or more of its components. In spite of the considerable cost of cryogenic operations, the procedure has been employed commercially for the separation of ethylene from other gaseous materials such as ethane and methane.

Our copending application Ser. No. 335,012 filed Feb. 23, 1973, describes methods for separating materials, e.g. aliphatically-unsaturated hydrocarbons, from mixtures containing them, and these procedures involve the combined use of liquid barrier permeation and metal complexing techniques which can exhibit high selectivity factors. In the processes, the liquid barrier is an aqueous solution containing metal ions which will complex with the material to be separated, and the liquid barrier is employed in conjunction with a semi-permeable membrane which is essentially impermeable to the passage of liquid. Preferred systems of this type are concerned with semi-permeable membranes which can be used in systems in which the liquid barrier containing the complex-forming metal ions is at least partially within a hydrophilic, semi-permeable film membrane. When operating in this manner, there is no need to maintain contact of the film with a separate or contiguous aqueous liquid phase during the process, thereby facilitating the use of a greater variety of semi-permeable members as far as physical configuration is concerned. Thus, the membranes can be designed without the hindrance of having to provide a separate liquid phase adjacent the film, and this may enable the use of film configurations having a greater surface or contact area.

In systems for conducting separations in which the aqueous liquid is disposed as a distinct liquid phase on the feed side of the semi-permeable membrane, there is the disadvantage of having to introduce the hydrocarbon mixture into the liquid phase, thereby reducing the effective rate or selectivity of the separation. Alternatively, the aqueous liquid phase has been held in contact with a semi-permeable membrane by absorbing the liquid in a porous solid such as filter paper, and holding the wet paper next to the semi-permeable membrane in, for instance, a sandwich-type cell construction. The physical limitations of this system make it unattractive, especially since the sandwich construction cannot easily be made in shapes which afford a sufficiently high surface area of film to provide good separation rates. Thus, the flow or separation capacity of these systems may make them economically less advantageous than other types of operations. The use of semi-permeable membranes having the liquid barrier within the film overcomes these disadvantages to a considerable extent, and offers high separation rates for a given investment in equipment. Moreover, the latter procedure avoids the necessity for maintaining a separate liquid aqueous phase in the system, and contact of the aqueous phase and the feed mixture containing the aliphatically-unsaturated hydrocarbon to be separated can thereby be facilitated. The film membranes can thus be essentially homogenous materials which are suitable for forming into various shapes, and the membranes may be formed by, for instance, extrusion and can be made into hollow fiber membranes. These fibers are preferred membrane configurations because they have the advantages of high surface area per unit volume, thin walls for high transport rates, and high strength to withstand substantial pressure differentials across the membrane or fiber walls. Sandwich membranes cannot readily be fabricated into the hollow fiber form.

In copending application Ser. No. 335,012, there is described the manufacture of membranes by dissolving a film-forming material, such as a nylon polymer, and a hydrophilic polymer, such as polyvinyl alcohol (PVA) in a solvent, and casting the solvent into the desired membrane. Problems arise in this procedure which are overcome by the present invention. One of the difficulties in fabricating membranes comprising a mixture of nylon and PVA lies in finding a suitable solvent for forming the mixed polymer composition into a film. The two best solvents, dimethyl sulfoxide and formic acid, have definite disadvantages. Dimethyl sulfoxide must usually be heated to make a film-forming solution, and since formic acid reacts with the PVA, saponification is necessary to convert the resulting polyvinyl formate back to PVA. The present invention overcomes the problems of finding solvents suitable for both polymers, because the films are made from an aqueous dispersion of nylon having dissolved therein a cross-linking agent, and PVA. The PVA and cross-linking agent are then reacted to fuse the polymer aggregates and provide the desired membrane.

Another problem arising from mixing nylon and PVA to form the membrane occurs during use. Over prolonged use of the membrane, the polyvinyl alcohol may be partially leached out of the film by the diffusing penetrant gases. The leaching results in a decrease in the hydrophilicity and, hence, in the effectiveness of the membrane. The chemical fusing by cross-linking of the polyvinyl alcohol, rather than a mere physical attachment, results in a membrane which has exceptional strength and is more resistant to penetrant gas leaching. This, of course, means that over a period of prolonged use, the novel membrane continues to be effective in the gas separation process.

The polyvinyl alcohol employed in the method of this invention is water-soluble, and is readily dissolved in the aqueous nylon dispersion and an emulsion may be formed. The dispersion may contain optional non-polymerizable, hydrophilic agents, which can be added in addition to the PVA, such as glycol, glycerol, and propylene glycol. The PVA is employed in the dispersion and in the membrane in an amount sufficient to enhance the hydrophilic properties of the nylon, and may be generally up to about 75 weight percent or somewhat more of the composition based on the total nylon and PVA polymer. This amount is often at least about 5 weight percent for it to be sufficient to impart a significant property to the resulting film. Preferably, the polyvinyl alcohol and the nylon is each about 10 to 75 weight percent of their total amount, or the polyvinyl alcohol may be about 10 to 55 weight percent and the polyamide about 90 to 45 weight percent of their total.

The film-forming materials which are employed to provide one component of the semi-permeable film membranes used in the present invention are those having a polyamide as an essential constituent. The polyamide film-forming materials are generally known and have also been designated as nylons. These polymers are characterized by having a plurality of amide groups serving as recurring linkages between carbon chains in the product structure, and the polymers may be made by several procedures. Commonly, the polyamides are formed by reacting a polyamine and dicarboxylic acid or its derivative such as an ester, especially a lower alkyl ester having, for instance, about 1 to 4 carbon atoms in each ester group. Other reactions which may be employed to form the polyamides include the self-condensation of monoamino, monocarboxylic acids and the reactions of cyclic lactams. In any event, the polyamide products contain recurring amide groups as an integral part of the principal polymer chain. The polyamides are described, for instance, in the Kirk-Othmer, *Encyclopedia of Chemical Technology*, Second Edition, Volume 16, beginning at page 1, Interscience Publishers, New York, 1968. Among the typical structural formulas of the linear polyamides are $H_2NRNH(COR'CONHRNH)_nCOR'COOH$ and $H_2NRCO(NHRCO)_nNHRCOOH$, where R and R' represent primarily carbon-to-carbon chains between functional groups in the reactants, and $n$ represents the degree of polymerization or the number of recurring groups in the polymer chain. The polyamides which can be used in this invention are generally solid at room temperature, and have a molecular weight which makes them suitable for forming the desired film membranes. Polyamides of this type are described in, for instance, U.S. Pat. No. 3,355,409.

The carboxylic acids which may be used in forming the polyamides have an acyloxy group (—R—COO—) in their structure and the R member of this group is composed essentially of carbon and hydrogen and often contains about 6 to 12 carbon atoms. Such groups may be aliphatic, including cycloaliphatic, aromatic, or a mixed structure of such types, but such groups are preferably aliphatic and saturated with respect to carbon-to-carbon linkages. These R groups may preferably have straight chain carbon-to-carbon or normal structures. Among the useful dicarboxylic acid reactants are adipic acid, sebacic acid, azelaic acid, isophthalic acid, terephthalic acid, and the methyl esters of these acids.

The polyamines employed in making the polyamide film-forming membranes generally have at least two non-tertiary, amino nitrogen atoms. These nitrogen atoms may be primary or secondary in configuration, although amines having at least two primary nitrogen atoms are preferred. The polyamines may also have both primary and secondary nitrogen atoms and the polyamines may contain tertiary nitrogen atoms. The preferred polyamine reactants have aliphatic, including cycloaliphatic, structures, and often have from 2 to about 12 carbon atoms. Also, the preferred polyamines are saturated and have straight-chain structures, although branched-chain polyamines can be used. Among the useful polyamines are ethylene diamine, pentamethylene diamine, hexamethylene diamine, diethylene triamine, decamethylene diamine and their N-alkyl substituted derivatives, for instance, the lower alkyl derivatives which may have, for instance, 1 to 4 carbon atoms in each alkyl substituent.

The cross-linking agents used in the present invention comprise the polycarboxylic acids, preferably those having from 2 to about 12 carbon atoms. These acids are water-soluble at least to an extent sufficient to provide the desired cross-linking reaction. Among the polycarboxylic acids, the triacids and especially the saturated diacids are preferred. Included among these are the aliphatic polycarboxylic acids, including oxalic acid, citric acid, maleic acid, malonic acid, and the like. Particularly good results are obtained using oxalic acid as the cross-linking agent.

The preferred method of forming the membranes of this invention comprises adding the cross-linking agent to the aqueous dispersion of PVA and nylon of fine particle size, formed by dissolving the PVA in a nylon-in-water dispersion, before the film is formed. Upon being formed, the film can be subjected to heat treatment, and the inclusion of the cross-linking agent in the mixture before the film is formed permits the cross-linking reaction to be enhanced by the subsequent heat treatment. The temperatures used should be sufficient to enhance the cross-linking reaction to the desired degree, but not such as to affect the membrane detrimentally. The amount of cross-linking agent used may depend upon which agent is chosen, the amount and molecular weight of the polyvinyl alcohol present in the mixture, and the degree of completion of the cross-linking reaction desired. The amount of cross-linking agent generally used is from about 1 to about 100 weight percent, and preferably from about 5 to about 60 weight percent, based on the weight of PVA.

After the film is formed and cross-linking is completed, the films can be impregnated with the metal component which contains ions capable of forming a complex with at least one of the components desired to be separated from a mixture. These ions may, as an alternative method, be mixed with the polymer constituents prior to formation of the film.

In the present invention, the metals in the film or in the liquid barrier solution, which metals may serve in the form of metal-containing cations to separate a component from a mixture through the formation of metal complexes or desired properties, include, for instance, the transition metals of the Periodic Chart of Elements having atomic numbers above 20. Included in these metals are those of the first transition series having atomic numbers from 21 to 29, such as chromium, copper, especially the cuprous ion, manganese and the iron group metals, e.g., nickel and iron. Others of the useful complex-forming metals are in the second and third transition series, i.e., having atomic numbers from 39 to 47 or 57 to 79, as well as mercury, particularly as the mercurous ion. Thus, we may employ noble metals such as silver, gold and the platinum group, among which are platinum, palladium, rhodium, ruthenium and osmium. The useful base metals of the second and third transition series include, for example, molybdenum, tungsten, rhenium and the like. Various combinations of these complex-forming metals may also be employed in this invention, either in the presence or absence of other non-metal or non-complexing metal components.

The metal is provided in the film or in aqueous liquid barrier of the separation system in a form which is soluble in this liquid. Thus, the various water-soluble salts of these metals can be used such as the nitrates and halides, for instance, the bromides and chlorides, fluoborates, fluosilicates, acetates, carbonyl halides or other salts of these metals which can serve to form the desired water-soluble complexes when the film is in contact with water. The metal salts should not react with any components of the chemical feedstock used in the separation procedure to form an isoluble material which could block the film membrane or otherwise prevent the separation of a component from the feedstock. Also, in a given system, the metal is selected so that the complex will readily form, and yet be sufficiently unstable, so that the complex will decompose and the dissociated material leave the liquid barrier, thereby providing a greater concentration of the material to be separated from the exit side of the membrane than is in the feed. The concentration of the metal ions in the film or liquid barrier may be rather low and still be sufficient to provide an adequate complexing rate so that excessive amounts of the semi-permeable membrane surface will not be needed to perform the desired separation. Conveniently, the concentration of the complex-forming metal ions in the aqueous solution forming the liquid barrier is at least about 0.1 molar and is preferably about 0.5 to 12 molar. Advantageously, the solution is less than saturated with respect to the complex-forming metal ions to insure that essentially all of the metal stays in solution, thereby avoiding any tendency to plug the film membrane and destroy its permeability characteristics.

When the complexing ions in the liquid barrier employed in this invention include cuprous ions, ammonium ions can be used to provide copper ammonium complex ions which are active to form a complex with the material to be separated by the use of the film. We preferably supply about equimolar amounts of cuprous and ammonium ions, although either type of ions may be in excess. The ammonium ions can be provided in various convenient ways, preferably as an acid salt such as ammonium chloride or as ammonium hydroxide or ammonium carbonate. In order to enhance the selectivity of the copper ammonium ion complex in the separation of this invention, we may also make the film and thus the liquid barrier solution more acidic, by, for instance, providing a water-soluble acid such as a mineral acid, especially hydrochloric acid in the film or liquid barrier solution. Preferably, the pH of the liquid barrier in this form of the invention is below about 5 with the acid in the solution. Since silver may form undesirable acetylides with acetylenes, the copper ammonium complex may be a more attractive complexing agent when it is desired to use the film to separate acetylenes from various mixtures.

Instead of supplying only a noble metal for complexing the material to be separated in the process of this invention, we may also employ mixtures of noble metal and other cation-providing materials. A portion of the noble metal may be replaced by non-noble metal or ammonium components. Accordingly, the total of such ion-forming materials in the film or in the liquid barrier may be composed of a minor or major amount of either the noble metal or the non-noble metal, ammonium or other components. Solutions having a major amount of the non-noble metal, ammonium or other cation-providing materials not containing a noble metal will generally be less expensive, and, accordingly, the noble metal may be as little as about 10 molar percent or less of the total cation-providing material in the solution. To reduce expenses at least about 10 molar percent, preferably at least about 50 molar percent, on a cation basis, of the total cation-providing material may be other than noble metal. The non-noble or base metals are preferably of Groups II to VIII of the Periodic Chart of Elements, and especially those in the fourth and fifth periods, aluminum and magnesium. Zinc and cuprous ions are preferred ones among these non-noble or base metal components. The various metals may be provided in the liquid barrier in the form of any suitable compound, such as the acid salt forms mentioned above with respect to the noble metals.

The amount of water in the liquid barrier employed in this invention may be a minor portion of the liquid phase, but preferably is a major portion of even essentially all of the liquid, on a metal salt-free basis. Thus, small or minor amounts of water, say as little as about 5 weight percent, on a salt-free basis in the liquid phase may serve to provide significant transport for the material to be separated across the liquid barrier. Any other liquid present in the barrier is preferably water-miscible and should be chosen as not to have a substantial deleterious effect on the separation to be accomplished. The liquid barrier may also contain a hygroscopic agent, e.g., in a minor amount, to improve the wetting or hydrophilic properties of the liquid and provide better contact with the feed gas.

In the system of the present invention, the amount of complex-forming metal in the semi-permeable membrane may vary considerably, but is sufficient to accomplish the desired separation. Often, this is a minor amount, say, about 1 to 50 weight percent, of the weight of the membrane on a non-aqueous basis, preferably about 5 to 25 weight percent. A suitable procedure for placing the solution of complex-forming metal in the semi-permeable film is by contacting the film with the solution and exerting a differential pressure across the solution and film. Thus, the pressure behind the solution is greater than that on the opposite side of the film, and as a result, the solution is forced into the film under pressure. Conveniently, the pressure on the solution is above atmospheric, and the opposite side of the film is essentially at atmospheric pressure. The pressure differential need not be large, for instance, it may only be at least about 5 or 10 psi, and it should not be so great that the film is ruptured. This procedure could also be used to reactivate films which have been used for very long periods of time to the point where they have lost selectivity.

The membrane containing the complex-forming metal may be handled and transported in an essentially non-aqueous form or with some water therein, for instance, an insufficient amount of water to be effective in the separation. In such case, water would be added to the membrane to give a film bearing sufficient water to be useful in performing the separation process of the invention. During use of the membrane, the amount of water present is preferably less than that which gives a substantial distinct or separate aqueous phase on the feed inlet side of the membrane. The film membrane can be wetted initially, and if it has a tendency to dry during use, additional water can be placed in the film while it is used on-stream in the separation, for instance, by inclusion of moisture in the gaseous feed charged to the system. Alternatively, but less advantageously, the operation can be stopped for addition of water to the film. The water could be added at intervals by stopping the feeding of the gaseous mixture to the system, and charging water to the membrane at such times. In any event, care should be taken to insure that the film membrane during use is not so dry that it will exhibit non-selective permeability to the material to be separated from the feed, and will thereby not serve to separate a product having an increased concentration of the desired ingredient.

The film membranes employed in the process of this invention are of the essentially water-insoluble, hydrophilic, semi-permeable type. In the absence in the film of the liquid containing the complex-forming ions, the film is generally not adequately selective with respect to the passage of or permeation by the material to be separated to perform the desired separation at the desired rate. Often, the film is permeable to essentially all of the components in the gaseous feedstock used in this invention. However, by having the film contain sufficient aqueous liquid to form a barrier, the simple diffusion of gas through the film is reduced or prevented, and the components of the feed stream must, therefore, traverse the film primarily by becoming part of, and then being separated from, the aqueous liquid phase contained in the film. Thus, in the absence of the complexing metal ion in the aqueous medium, there could be a slight separation effected by the use of water as the liquid medium since the individual components in the gas may exhibit differing solubilities in water. In the method of the present invention, however, the selectivity of the separation is greatly increased due to the presence of the complex-forming metal ions in the aqueous barrier medium. Also, during use in the process of this invention, the film has a sufficient amount of the aqueous medium so that adequate metal ions are in solution, or at least react as if they are, to perform the desired separation.

The film membranes which can be employed in this invention are preferably self-supporting and have sufficient strength not to require any additional supporting material on either of its sides during use. With some films, however, it may be necessary, advantageous or convenient to provide adequate support such as additional film or sheet-like materials on one or both sides of the film membrane. These supporting structures are frequently very thin materials and may be permeable to both liquids and gases and not serve a separating function with respect to any component of the feed stream. Alternatively the supporting film may be permeable to gases, but not to liquids.

The film membranes of this invention may have a thickness of up to 30 mils or more. Preferably the thickness is up to about 10 mils. The films are sufficiently thick to avoid rupture during use and generally have a thickness of or at least about 0.001 mils. The film is sufficiently hydrophilic to hold the liquid barrier solution at least partly within the membrane. This hydrophilic property is present in the film membrane due to the character of both the polyamide or nylon polymer and the cross-linked hydrophilic polymer. The cross-linked polyvinyl alcohol is a hydrophilic agent and other hydrophilic agents may also be present. The optional non-polymeric hydrophilic agents which may be added include the polyhydric alcohols such as ethylene glycol, glycerol, and propylene glycol. The film membrane may be considered sufficiently hydrophilic to be useful if it absorbs at least about 5 weight percent of water when immersed in distilled water for one day at room temperature and pressure.

The metal-containing, semi-permeable films made by the procedure of the present invention may be employed, for instance, to separate one or more unsaturated hydrocarbons by the liquid barrier-complex-forming technique having the barrier in the film. Although the aliphatically-unsaturated hydrocarbon products thus provided may be quite pure materials, for instance, of greater than 99% purity, the separation procedure may be used merely to provide a significant increase in the concentration of a given aliphatically-unsaturated hydrocarbon in a mixture with other components of the feedstock.

The process can be employed to separate various aliphatically-unsaturated hydrocarbons from other ingredients of the feed mixture providing at least one of the aliphatically-unsaturated hydrocarbons exhibits a complexing rate or transfer rate across the liquid barrier in the film that is greater than at least one other dissimilar or different component of the feedstock. Quite advantageously, the system can be used to separate aliphatically-unsaturated hydrocarbons from other hydrocarbons which may be aliphatically-saturated or aliphatically-unsaturated, or from non-hydrocarbon materials, including fixed gases such as hydrogen. The feed mixture may thus contain one or more paraffins, including cycloparaffins, mono- or polyolefins, which may be cyclic or acyclic, and acetylenes or alkynes, and the mixture may include aromatics having such aliphatic configurations in a portion of their structure. Often, the feed mixture contains one or more other hydrocarbons having the same number of carbon atoms as the unsaturated hydrocarbon to be separated or only a one carbon atom difference. Among the materials which may be separated according to this invention are ethylene, propylene, butenes, butadiene, isoprene, acetylene and the like.

In the method, the mixture containing the aliphatically-unsaturated hydrocarbon to be separated may be essentially in the gaseous or vapor phase when in contact with the liquid barrier having dissolved therein one or more metal ions which form a complex with the unsaturated hydrocarbon. The liquid barrier is within, and thus in contact with the semi-permeable membrane which may be permeable to the aliphatically-unsaturated hydrocarbon-containing mixture in the absence of the liquid barrier. The membrane can be said to immobilize the liquid barrier within the membrane. The liquid barrier may in essence be completely within the semi-permeable structure, and the liquid does not pass from the membrane to an excessive extent under the conditions of operation. The membrane is, however, selectively permeable in the presence of the liquid barrier to the component of the feedstock to be separated. Since there is little, if any, passage for the feedstock across the separation zone except by becoming part of or reacting with the liquid barrier, this liquid barrier controls the selectivity of the liquid barrier-semi-permeable membrane combinations.

The liquid barrier contains sufficient water and soluble metal ions to form a suitable complex with at least one aliphatically-unsaturated hydrocarbon component of the feed subjected to the separation procedure. The metal ions readily form the complex upon contact with the feed, and, in addition, the complex dissociates back to the metal ion and an aliphatically-unsaturated hydrocarbon component of the complex, under the conditions which exist on the discharge side of the liquid barrier and semi-permeable membrane as employed in the process. The released aliphatically-unsaturated hydrocarbons exit the discharge side of the membrane and can be removed from the vicinity of the barrier and its supporting structure as by a sweep gas or through the effect of vacuum on this side of the barrier. Thus, the unsaturated hydrocarbon-metal complex forms and is decomposed in the complex metal ion-containing liquid barrier, and, as a result, the material passing through the barrier is more concentrated with respect to at least one aliphatically-unsaturated hydrocarbon component present in the feed stream.

Often, the reactivity of aliphatically-unsaturated hydrocarbons with the complexing metal ions in their order of decreasing activity goes from acetylenes or dienes to monoolefins, the aliphatically-saturated hydrocarbons and other materials present being essentially non-reactive. Also, different reactivities may be exhibited among the various members of a given type of aliphatically-unsaturated hydrocarbons. The process can thus be used to separate paraffins from monoolefins, diolefins or acetylenes; diolefins from monoolefins; or acetylenes from paraffins, monoolefins or diolefins; as well as to separate a given aliphatically-unsaturated hydrocarbon from another of such materials in its class where the members have differing complexing rates with or transport rates across the liquid barrier. The feed need only contain a small amount of aliphatically-unsaturated hydrocarbon, as long as the amount is sufficient so that the unsaturated material to be separated selectively reacts with the metal complex ions to a significant extent, and thus at least one other component of the feed is less reactive or non-reactive with the complex-forming metal ions.

The aliphatically-unsaturated materials of most interest with regard to separation have 2 to about 8 carbon atoms, preferably 2 to 4 carbon atoms. The separation of aliphatically-unsaturated materials from admixtures containing other gaseous materials, such as the separation of ethylene or propylene from admixtures with other normally gaseous materials, e.g., one or more of ethane, propane, and methane and hydrogen, is of particular importance. Frequently, such feed mixtures for the process contain about 1 to 50 weight percent ethylene, about 0 to 50 weight percent ethane and about 0 to 50 weight percent methane. Another process that may be of special significance is the separation from ethylene of minor amounts of acetylene.

The partial pressure of the aliphatically-unsaturated component of the feed at the input side of the liquid barrier used in the separation is greater than the partial pressure of this unsaturated hydrocarbon on the discharge or exit side of the liquid barrier-semi-permeable membrane composite. This pressure drop of the unsaturated hydrocarbon to be separated may often be at least about 0.5 pound per square inch, and is preferably at least about 20 psi, although the pressure drop should not be so great that the liquid barrier is ruptured or otherwise deleteriously affected to a significant extent. Conveniently, the total pressure of the feed is up to about 1000 pounds per square inch. The discharge partial pressure of the unsaturated hydrocarbon can preferably be controlled by subjecting the exit side of the liquid barrier to the action of a sweep gas that may be essentially inert to forming a complex with the metal ions in solution in the liquid barrier. The sweep gas picks up the discharged aliphatically-unsaturated components, and the sweep gas may be selected so that it can be readily separated from the aliphatically-unsaturated hydrocarbon material if that be necessary for the subsequent use of the unsaturated hydrocarbon. Unless a reaction with the separated hydrocarbon is desired, the sweep gas should be relatively inert therewith and may be, for instance, butane, carbon dioxide or the like.

The temperature across the liquid barrier-semi-permeable film composite employed in the separation procedure can be essentially constant or it may vary, and decomposition of the metal-unsaturated hydrocarbon complex can be effected primarily by the drop in partial pressure of the aliphatically-unsaturated hydrocarbon on the exit side of the liquid barrier compared with the partial pressure on the feed side. Conveniently, the temperature of the liquid barrier may be essentially ambient, especially in the case of feedstocks that are gaseous at this temperature and the pressure employed on the feed side of the liquid barrier. The temperature of the liquid barrier may, however, be reduced or elevated from ambient temperature. Often, the temperature may be up to about 100°C., and elevated temperatures may even be desired to put the feedstock in the gaseous or vapor phase. Neither the temperature nor the pressure used should, however, be such as to destroy the difference in transport rate across the liquid barrier, semi-permeable film composite of the aliphatically-unsaturated hydrocarbons whose separation is sought, compared with that of the other components of the feed. The conditions should also not be such that physical disruption of the liquid barrier or any other significant malfunction results.

The methods and products of this invention are described further by the following examples. Unless otherwise indicated, the percentages given are on a weight basis.

EXAMPLE 1 (FILM A)

To 50 g. of duPont Elvamide PB-3-1521 nylon in water (50% nylon) dispersion is added 25.5 g. of a 15% aqueous solution of polyvinyl alcohol, 2 g. of glycerol, and 1.8 g. of oxalic acid. The mixture is stirred in a Waring Blender until thoroughly mixed. The mixture is then placed in a vacuum dessicator and a partial vacuum applied to degas the mixture. This mixture is used to cast Film A.

the membrane. On the outlet side of the cell and membrane, another annular arrangement is used whereby a purging gas, helium, passes into the outlet side of the cell and sweeps away gases which have permeated the membrane. The helium passes in through the smaller tube and carries away the permeated or separated gases through the surrounding annular passage. The test cell is divided into upper and lower compartments locating the membrane horizontally across the cell. The cell internal cross-sectional area is 3.8 cm$^2$ and the cross-section is fully covered by the film membrane in a manner to provide an effective membrane area of 2.2 cm$^2$. The main body of the cell has a height of 41 mm. and a gas outlet at each end. A feed inlet tube enters the upper end of the cell and opens about 5 mm. above the film, and a sweep gas inlet tube enters the lower end of the cell and opens about 1 mm. below the film.

A mixed gas of methane, ethane, and ethylene is humidified at 125° F. and is supplied to the cell at 10 ml./min. under a pressure of 30 psig. The permeate through the membrane is purged from the cell with a 10 ml./min. stream of helim. The permeate composition and permeation rate are determined for each film tested. These results are summarized in Table I below.

TABLE I

| Membrane Composition | Ethylene Separation With Nylon-Cross-Linked PVA Membranes Permeate Composition (wt.% He-free) | | | S | P ml/cm$^2$-min |
| --- | --- | --- | --- | --- | --- |
| | Methane | Ethylene | Ethane | | |
| Feed Gas Composition | 18.5 | 50.8 | 30.6 | — | — |
| Film A, Swollen with Water | 18.3 | 50.6 | 31.1 | 0.97 | 0.0002 |
| Film A With 6 M AgNO$_3$ | 0.13 | 99.64 | 0.23 | 273 | 0.033 |
| Film B, Swollen with Water | 5.3 | 78.6 | 16.1 | 3.4 | 0.001 |
| Film B with 6 M AgNO$_3$ | 0.45 | 99.21 | 0.34 | 121 | 0.0096 |

$$S = \left(\frac{[\text{Ethylene}]}{[\text{Methane} + \text{Ethane}]}\right)_{\text{Permeate}} \times \left(\frac{[\text{Methane} + \text{Ethane}]}{[\text{Ethylene}]}\right)_{\text{Feed}}$$

EXAMPLE 2 (FILM B)

To 100 g. of duPont Elvamide PB-3-1521 nylon in water (50% nylon) dispersion is added 50 g. of a 15% PVA solution. To a 20 ml. aliquot of the resultant mixture is added 1.0 g. of oxalic acid. This mixture is stirred thoroughly and then degassed. The degassed mixture is used to cast Film B.

Films are cast from each of the mixtures of Examples 1 and 2 with a 6 mil. doctor knife onto clean 4 × 8 inch glass slides. After drying, each film is heated to 165° C. for 5 minutes, then heated at 125° C. for 3 hours. This treatment is carried out to first fuse the nylon aggregate particles into a continuous film and then to effect thermal cross-linking. The resulting films are designated A and B, respectively. The films are tested for their selectivity and permeability to ethylene in a hydrocarbon gas mixture. Both films are tested as water-swollen films, and as films saturated with a 6M AgNO$_3$ solution.

For testing, a closed glass cell is used in which the membrane film is placed so as to divide the cell into an inlet and an outlet side. A gas inlet tube passes through the cap of the cell and extends into the cell ending near the membrane. A tube of larger diameter surrounds the inlet or feed tube forming an annular passage which permits exhaust of those gases which do not permeate It is clear from the table that the membranes of the present invention exhibit extraordinary selectivity in the separation procedure when activated with the complexing-forming component, as shown by a comparison of the selectivity factor S.

It is claimed:

1. In a method for separating a gaseous material from a mixture which comprises contacting said mixture containing said material with a first side of an essentially solid, water-insoluble, hydrophilic, semi-permeable membrane having therein an aqueous liquid barrier having ions which combine with said material to form a water-soluble complex, the partial pressure of said material on a second side of said semi-permeable membrane being sufficiently less than the partial pressure of said material in said mixture to provide separated material on said second side of said semi-permeable membrane, and removing said separated material from the vicinity of said second side of said semi-permeable membrane, said separated material having a transfer rate across said liquid barrier that is greater than at least one other component of said mixture, the improvement which comprises employing as said semi-permeable membrane a polymer film comprising: (a) nylon, and (b) polyvinyl alcohol cross-linked with water-soluble polycarboxylic acid.

2. In a method for separating aliphatically-unsaturated hydrocarbon from a mixture which comprises contacting said mixture containing said aliphatically-unsaturated hydrocarbon with a first side of an essentially solid, water-insoluble, hydrophilic, semi-permeable membrane having therein an aqueous liquid barrier having ions which combine with said aliphatically-unsaturated hydrocarbon to form a water-soluble complex, the partial pressure of said aliphatically-unsaturated hydrocarbon on a second side of said semi-permeable membrane being sufficiently less than the partial pressure of said aliphatically-unsaturated hydrocarbon in said mixture to provide separated aliphatically-unsaturated hydrocarbon on said second side of said semi-permeable membrane, and removing said separated aliphatically-unsaturated hydrocarbon from the vicinity of said second side of said semi-permeable membrane, said separated aliphatically-unsaturated hydrocarbon having a transfer rate across said liquid barrier that is greater than at least one other component of said mixture, the improvement which comprises employing as said semi-permeable membrane a polymer film comprising: (a) nylon, and (b) polyvinyl alcohol cross-linked with water-soluble polycarboxylic acid.

3. The method of claim 2 wherein said membrane comprises about 10 to about 75% by weight of cross-linked polyvinyl alcohol based on the total weight of the polyvinyl alcohol and nylon.

4. The method of claim 3 wherein the polyvinyl alcohol is cross-linked with about 5 to about 60% by weight polycarboxylic acid based on the polyvinyl alcohol.

5. The method of claim 4 wherein said polyvinyl alcohol is dicarboxylic acid cross-linked polyvinyl alcohol.

6. The method of claim 5 wherein the separated hydrocarbon is ethylene.

7. The method of claim 6 wherein said metal is silver.

8. The method of claim 7 wherein said dicarboxylic acid is oxalic acid.

* * * * *